US011379731B2

(12) United States Patent
Hill et al.

(10) Patent No.: US 11,379,731 B2
(45) Date of Patent: Jul. 5, 2022

(54) RELATING COMPLEX DATA

(71) Applicant: The Regents of the University of California, Oakland, CA (US)

(72) Inventors: Erik Hill, La Jolla, CA (US); Sheldon Brown, La Jolla, CA (US); Wesley Hawkins, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/260,993

(22) PCT Filed: Jul. 16, 2019

(86) PCT No.: PCT/US2019/042058
§ 371 (c)(1),
(2) Date: Jan. 15, 2021

(87) PCT Pub. No.: WO2020/018576
PCT Pub. Date: Jan. 23, 2020

(65) Prior Publication Data
US 2021/0248480 A1 Aug. 12, 2021

Related U.S. Application Data

(60) Provisional application No. 62/698,723, filed on Jul. 16, 2018.

(51) Int. Cl.
*G06N 5/02* (2006.01)
*G06F 16/24* (2019.01)
(Continued)

(52) U.S. Cl.
CPC ............. *G06N 3/126* (2013.01); *A63F 13/69* (2014.09); *G06F 9/455* (2013.01); *G06F 16/245* (2019.01);
(Continued)

(58) Field of Classification Search
CPC . G06N 3/126; A63F 13/69; G06F 9/45; G06F 16/245; G06Q 30/0201; G16H 50/70; G16H 10/60; G16H 50/50
(Continued)

(56) References Cited

U.S. PATENT DOCUMENTS

2004/0133355 A1  7/2004  Schneider
2005/0187846 A1  8/2005  Subbu et al.
(Continued)

OTHER PUBLICATIONS

Biswas et al. "Automated Iterative Tolerance Value Allocation and Analysis" ASU, Aug. 2016. 95 pages.
(Continued)

*Primary Examiner* — Brandon S Cole
(74) *Attorney, Agent, or Firm* — Perkins Coie LLP

(57) ABSTRACT

A data analysis and processing method includes forming an initial assembly of datasets comprising multiple entities, where each entity is a collection of variables and relationships that define how entities interact with each other, simulating an evolution of the initial assembly by performing multiple iterations in which a first iteration uses the initial assembly as a starting assembly, and querying, during the simulating, the evolution of the initial assembly, for datasets that meet an optimality criterion.

20 Claims, 13 Drawing Sheets

(51) Int. Cl.
*G06N 3/08* (2006.01)
*G06N 5/00* (2006.01)
*G06N 3/12* (2006.01)
*A63F 13/69* (2014.01)
*G06F 16/245* (2019.01)
*G06F 9/455* (2018.01)
*G16H 50/70* (2018.01)
*G06Q 30/02* (2012.01)

(52) U.S. Cl.
CPC ......... *G06Q 30/0201* (2013.01); *G16H 50/70* (2018.01)

(58) Field of Classification Search
USPC ........................................................ 706/1–62
See application file for complete search history.

(56) References Cited

U.S. PATENT DOCUMENTS

| | | |
|---|---|---|
| 2013/0332195 A1 | 12/2013 | Galuten |
| 2014/0222847 A1 | 8/2014 | Stivoric et al. |
| 2015/0243176 A1* | 8/2015 | Zaslavsky ............ G06F 3/04842 434/322 |
| 2017/0011292 A1* | 1/2017 | Thompson ............. G06N 3/126 |
| 2017/0364812 A1* | 12/2017 | Thompson ............. G06N 3/126 |
| 2018/0082209 A1* | 3/2018 | Thompson ............. G06N 3/126 |
| 2019/0073591 A1* | 3/2019 | Andoni .................. G06N 3/084 |
| 2019/0205773 A1* | 7/2019 | Ackerman ........... G06Q 10/067 |

OTHER PUBLICATIONS

Cockfield et al. "MOBBED: a computational data infrastructure for handling large collections of event-rich time series datasets in MATLAB" Neuroinformatics, Oct. 10, 2013. 35 pages.

Hitch et al. "Spherical: an iterative workflow for assembling metagenomic datasets" BMC Bioinformatics, 2018, 8 pages.

ISA, International Search Report and Written Opinion for International Application No. PCT/US2019/042058, dated Oct. 7, 2019. 10 pages.

EPO, Extended European Search Report for European Application No. 19838637.7. dated Mar. 11, 2022. 10 pages.

* cited by examiner

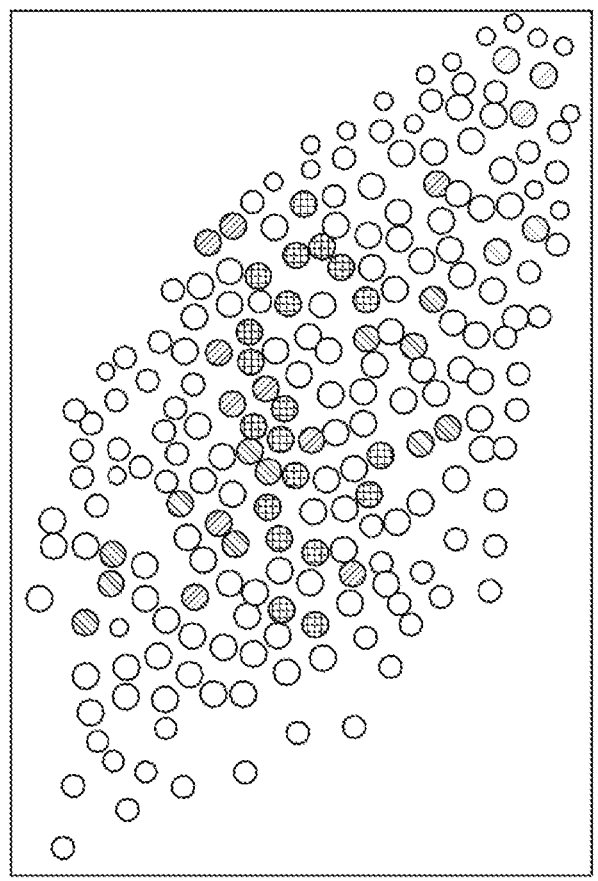
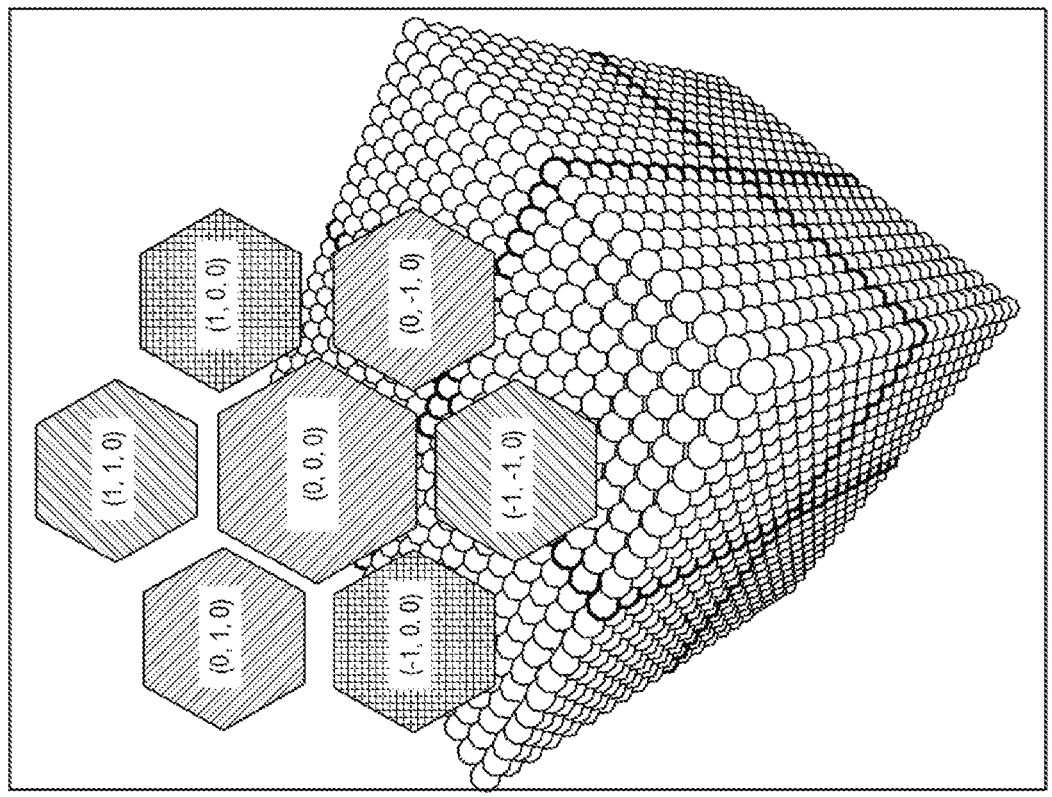
FIG. 5

Early Assemblies constructed using the rigid closest packing system, displaying the organic aesthetic of a system that is otherwise fundamentally Euclidian in its construction

RELATING COMPLEX DATA

PRIORITY CLAIM

This present document is a 371 National Phase Application of International Application No. PCT/US2019/042058, filed on Jul. 16, 2019, which claims the benefit of priority of U.S. Provisional Patent Application Ser. No. 62/698,723 entitled "RELATING COMPLEX DATA," filed on Jul. 16, 2018. The entire contents of these documents are incorporated by references into the present document.

STATEMENT REGARDING FEDERALLY SPONSORED RESEARCH OR DEVELOPMENT

This invention was made with government support under grant IIP-1439664 awarded by the National Science Foundation (NSF). The government has certain rights in the invention.

TECHNICAL FIELD

This patent document relates to the fields of artificial intelligence and database processing.

BACKGROUND

In the digital age, an ever increasing amount of digital data is being generated by human activity, sensors, and computational process, and is being stored and analyzed by computers. Data capture and analysis is often an important step in many advances in basic sciences, computer technologies, financial industry, healthcare, and for solving many real-life problems.

SUMMARY

Disclosed are devices, systems and methods for analysis of complex data.

In one example aspect, a computer-implemented data processing method is disclosed. The method includes forming an initial assembly of datasets and algorithmic relationships by instantiating in a colony of assemblies that have a range in variations of their dataset and algorithmic conditions, associating at least one contextual condition with the colony, comparing individual assemblies in the colony against each other and with the at least one contextual condition to find optimizations provided by the individual assemblies, simulating an evolution of the initial assembly by performing multiple iterations in which a first iteration uses the initial assembly as a starting assembly, and providing, based on a query during the evolution of the initial assembly, datasets that meet an optimality criterion. The evolution is simulated by causing the starting assembly to evolve by having each dataset in the starting assembly to (1) interact with other datasets in the starting assembly using corresponding algorithmic relationships; or (2) change values of at least some datasets using a randomization technique, culling, at an end of an $n^{th}$ iteration, assemblies in the colony that failed to meet a target objective function for the $n^{th}$ iteration, and replacing, selectively based on finality of the multiple iterations, the starting assembly to include remaining datasets and algorithmic relationships after the culling.

In another example aspect, a computer-implemented data processing method includes forming an initial assembly simulating an evolution of the initial assembly by performing multiple iterations in which a first iteration uses the initial assembly as a starting assembly, and querying, during the simulating, the evolution of the initial assembly, for datasets that meet an optimality criterion. The simulation includes causing the starting assembly to evolve by having the multiple entities in the starting assembly (1) interact with other entities in the starting assembly using the relationships; or (2) change values of variables using a randomization technique, culling, at an end of an iteration; a number of multiple entities that fail to meet a target objective function for that iteration, and replacing, selectively based on finality of the multiple iteration, the starting to include remaining entities after the culling.

In another aspect, a computer system that includes one or more computing platforms may be configured to implement the above-described method.

In yet another aspect, the above-described method may be embodied in the form of computer-executable code and stored on a storage medium.

In yet another aspect, a visualization method for displaying ongoing progress of the simulations is disclosed.

Various embodiments may preferably implement the following features with respect to the methods described above.

Preferably, at least one of the multiple entities includes a collection of entities.

Preferably, the comparing is used to find particular optimizations provided by individual assemblies.

Preferably, a different target objective function is used for at least some iterations.

Preferably, the target objective function includes an energy function.

Preferably, the target objective function includes a uniqueness function.

Preferably, a different target objective function is used for at least some iterations.

Preferably, the operation of causing the starting assembly to evolve further includes creating new entities as a result of interaction between two of the multiple entities.

Preferably, at least some entities in the initial assembly correspond to a real-world attribute and wherein the forming the initial assembly of datasets includes forming the at least some entities by including fields of a database based associated with the real-world attribute.

Preferably, dataset matching is used for creating new entities.

Preferably, dataset assemblies may interact based on meeting a compatibility criterion.

Preferably, culling may be performed using deviation from a template as a criterion.

These, and other, features and aspects are further disclosed in the present document.

BRIEF DESCRIPTION OF DRAWINGS

FIG. 5 shows examples of rigid grid structures and free-form structures while using integer representation for values used in various computer data structures.

DETAILED DESCRIPTION

Figure 1:
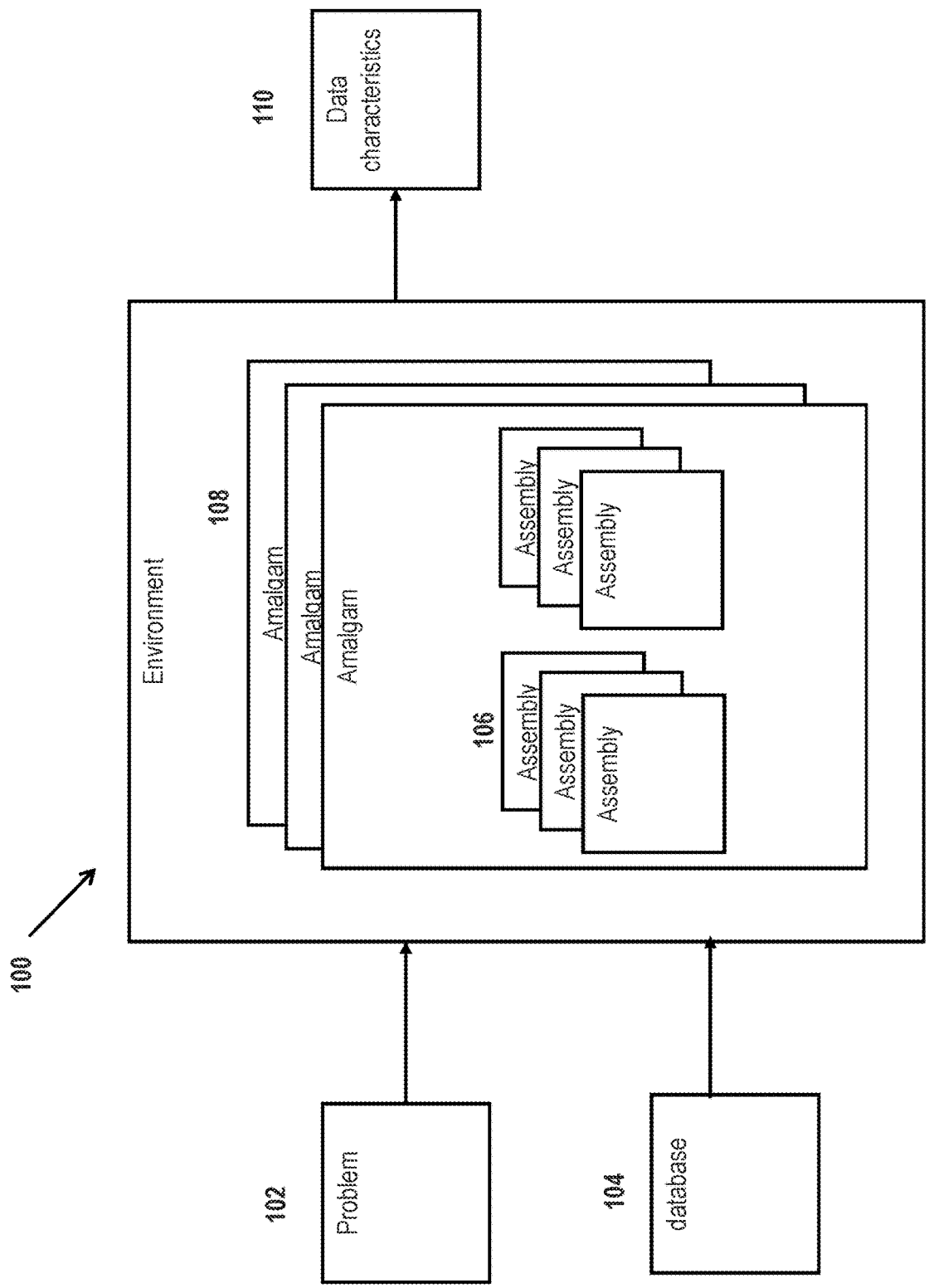
FIG. 1 is an example of a program execution environment.

In the recent years, practically every aspect of human life, and our understanding of all things, is being captured and stored as computer data. Examples of things that can be modeled or stored in the form of computer data include global weather patterns, interstellar data, natural ecosystems, financial data, and so on. New data is created, stored and analyzed in sports, finance, healthcare field, arts, law enforcement, e-commerce, science, news reporting, and so on. As the amount of data keeps growing, new computers are continually being developed to help with storage and analysis of this ever-growing amount of information.

For example, a law enforcement officer or a stock broker or a medical practitioner or a sports manager or a scientist may have a large amount of data at his fingertips and may be able to use today's tools that allow the user to sift through the data and retrieve useful data. However, one limitation such tools have is that the user will be able to retrieve only what he is looking for. The existing tools are inadequate in searching for patterns by learning correlations among data. For example, many modern databases today are very large, with easily upwards of 100s of millions of data entries. While simple query and search techniques or relational searches of databases is possible with many current tools, such tools do not provide additional insight into the database by having a computer learn similarities or differences among various data entries.

The present document discloses techniques that can be embodied into systems for complex data analysis. One way of looking at some embodiments is by using the metaphors of an evolving, multi-level artificial life environment to derive novel, optimized relationships between data and algorithmic functions. Some embodiments may include a synthetic system of encoding characteristics, and a set of rules akin to the chemistry and physics of an environment, provide the basis for creating increasingly complex emergent behavior.

In some disclosed embodiments, a collaborative agency is created between the impulses of the algorithmic systems and the means of their understanding through interaction and experimentation.

Some embodiments described in the present document relate to experimenting with the potential for emergent 'intelligence' through the assemblage and interactions of simple components.

Some embodiments disclosed in the present document relate to developing increasingly more complex systems of interactions, mimicking neural networks.

Some embodiments described in the present document relate to creating a multi-user gameplay experience that pushes the envelope of 'standard' multiplayer gaming through procedural and evolution-based generative gameplay.

Some embodiments implement methods for optimizing data and algorithmic relationships. For example, a method may include the ability to isolate different aspects of a colony of assemblies, which may be, for example, data grouping as described in the present document, based on specifying criteria for selecting one or more assemblies from the colony. These segregated assemblies can then be placed into contextual conditions that are any subset of the original contextual environmental conditions, including all aspects of the original, or subset aspects. In some embodiments, the subset of assemblies and the subset of the environmental context is run in the evolutionary scheme as a separate computational process and may be run on distinct hardware or on parallel threads of the same hardware as the original program. At any time during the implementation, assemblies that have developed on these alternative threads can be reintroduced back into the main computational system. Some embodiments may then check if more narrowly specified optimizations will provide value into the overall robustness of the colony behavior or be of higher optimality than colony members that have evolved in the larger environmental conditions.

An example of how the above-described techniques might work in relationship to the automobile design optimization is described next. A data analysis system may determine that a user of this system wants to design a car that is optimized for one aspect of its function such as traction. The system could evaluate designs that have emerged through the execution that might have a range of characteristics that the system may consider to be a good overall balance (acceleration, braking, cargo capacity, fuel efficiency, environmental impact, etc.). The system could select one or more of these candidates that have been evolved in the system that have responded to a very large number of contextual conditions and have out-competed with each other for particular success such as consumer desirability. The user could select candidates and create a limited fitness test for a characteristic such as "traction." The user may also create an environmental context in which traction conditions are the only consequential variance. The design evolution process could then vary such parameters as tire width, tire compounds, suspension system, number of wheels, aerodynamic effects, weight distribution, turning radius, center of gravity, etc. When the variations of these characteristics have reached some level of optimization, the successful candidate(s) can then be reintroduced into the larger set of contextual conditions with its broader or complete range of characteristics available to the evolutionary process.

Another example of the data analysis techniques can also be illustrated in the field of healthcare. An implementation may look for optimized relationships of hundreds of human behavior and physiological measurement by culling results from large scale health studies. The implementation can build a model of individuals that consist of components that have been measured, and then evolve these individuals with appropriate variances in individual traits to determine how they may affect health against the contextual conditions of the aggregated study data. Implementations can take individual simulated individuals or individual real world patients into their own process, and run independent evolutionary processes to see what kinds of behavioral, environmental and/or biometric changes would do to the overall health outcomes. These can be with the full context of the aggregate studies in total or on any subset of them.

Additional details and embodiments are now discussed for the complex data analysis techniques introduced above.

Brief System Overview

FIG. 1 depicts an example of a program execution environment 100. The environment 100 may be implemented using a single computer platform or using distributed computers such as a cloud computing network. The environment 100 may be constructed to solve a problem 102. Depending on the problem 102, entries of one or more databases 104 may be used during the implementation and simulations performed in the environment 100. Various examples of the problems 102 and formation of environments 100 are described throughout the present document.

The environment 100 may include a number of assemblies 106, some of which may be grouped together into corresponding amalgams 108. Thus, an amalgam 108 may include a number of assemblies 106. When solving a complex problem with multiple relationships among various database entries and their interplay with the desired solutions, a single environment 100 may include up to 10,000 (or more) assemblies, as further described in the present document.

Furthermore, while FIG. 1 does not explicitly depict a colony, this term could refer to a collection of assemblies, separate from their environment. For example, a colony together with its context(s) would be an amalgam. A colony of amalgams could be considered to be an environment. Thus, complex datasets may be organized in recursive structures with corresponding associated behavior attributes, as disclosed in the present document.

Examples of Assembly Schemes

Figure 2:
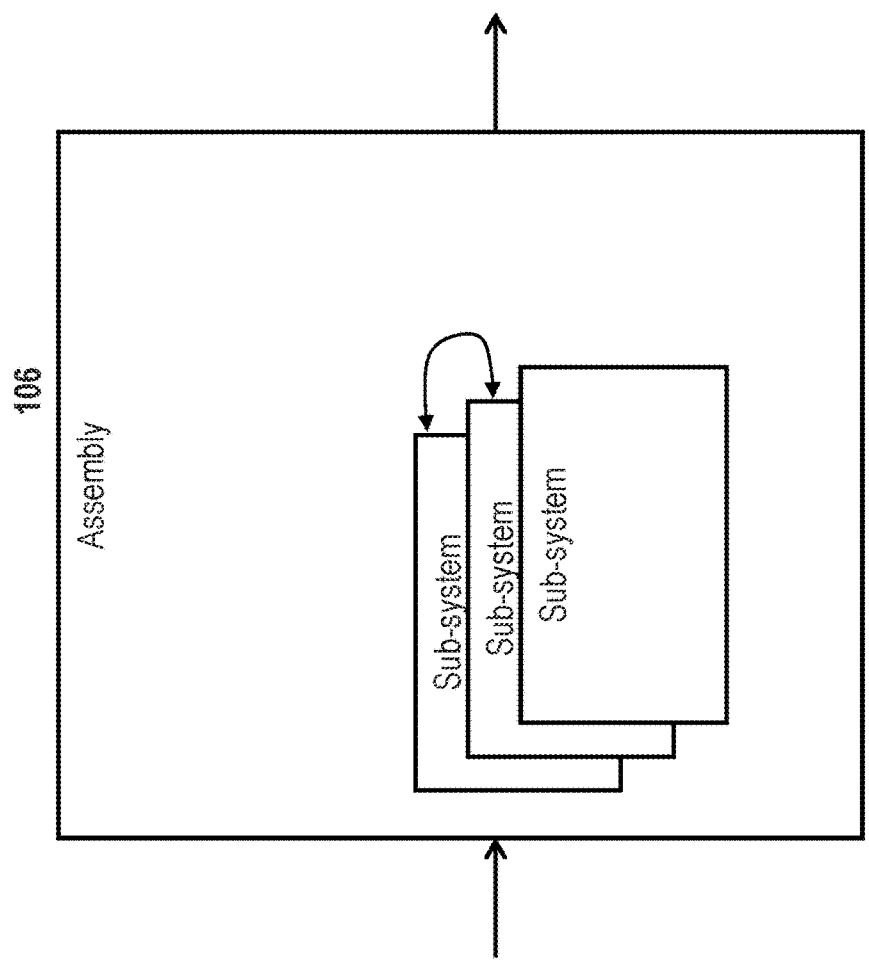
FIG. 2 is an example implementation of an Assembly behavioral platform of symbiotic computational systems.

FIG. 2 pictorially depicts an example implementation of an Assembly scheme 106. In an Assembly scheme 106, data and algorithms may be treated as traits and behaviors for artificial life organisms and exist in an environment that filters and selects the best performing variations between their possible states. Entities consist of many pieces of data in many algorithmic relationships between. Variations in the data and their algorithmic relationships are created through multiple methods, such as random changes (mutations) and inherited combinations from multiple parents (reproduction). Entities exist within a context of conditions which tests their overall robustness. These environmental conditions can be set to allow for a variety of testing scenarios for allowing entities to continue to exist and evolve as candidate solutions. High performing entities persist, while low performing solutions are culled. Over time, highly optimal solutions are created and can exhibit novelty in the relationships between data and algorithms that would be unlikely for a human designer to determine. The scale of data sets and any algorithmic relationships that they are involved in is theoretically without limits. However, we have focused on optimizing this process for data sets with up to 1000's of characteristics clustered in a variety of ways.

The Assembly system 106 works well with data that have morphological dependencies. An example of which would can be found in a describing the components of an automobile racing around a track whose time and distance traveled will be determined by the interrelationship between vehicle size and weight, engine power, aerodynamics, energy consumption, braking distance, tire composition, and many other factors, with each having their own subsets of details and variables. Additionally, different environmental conditions including such things as track shape, road surface and weather might favor different optimal solutions. An initial simulation model is created in which the overall problem is segmented into sub-systems which have specified relationships to other sub-systems and/or to the system defined at a particular scale of operation. In the example of the race-car, a tire would be a reasonable subsystem—with its variables of dimensions, compounds, tread type, inflation level. Some of those characteristics could have multiple characteristics, while others may only have a single value. The tire entity would be able to physically connect to other aspects of a meta-entity at a point and the characteristics of the connection would also be subject to variation and evolution. The sports car problem would continue to be broken down into a set of subsystems in this way. The level of detail of subsystems can be very deep, and can have nested entities. In this analogy, the environment of the track would also be specified with traits such as length, surface, weather, regularity, fuel availability, race conditions (time and/or length limits). The start of a simulation would be the random production of many possible variables at all states. An initial fitness function can be applied, in this case, it can be if the entity is able to produce an motion, with failures culled, and survivors producing a generation of offspring with random mutations—the number of offspring can vary and can be dependent on how well one does on the fitness function, perhaps in this case the one who was able to travel furthest produces a dozen (or a million) mutant offspring, with mutations rates that vary from very small amounts to large amounts (i.e. 0.01% to 10% of traits) in both the number and range of change possible in the traits. A fitness test can be applied again, in this case characterized by whether an entity makes it to a certain signpost. Those that do are able to reproduce; those that don't by a certain time are culled. The larger scale environmental condition is that of compute resource, computing the ongoing variations of solutions that aren't likely to produce viable solutions is a waste of the resource which should be applied to the most promising of solutions. However, keeping different approaches in play can lead to optimal solutions later on in the simulation as advantageous mutations come in to play at later stages. The nature of the condition being addressed can determine if an aggressive or passive culling strategy might make more sense, and in fact this approach itself can be subjected to the same evolutionary computing methodology as a higher level nesting of the underlying simulation.

The environmental interactions can also be aspects of the simulation. For instance, there may be certain kinds of resources that the entities vie for. In this case, a fuel resource can have limitations, after going a certain distance (and in a particular direction) the entity could find themselves taking on fuel. The amount they take on could have multiple implications, too much adds to the weight, too little and they entity might not have enough energy to continue. Fuel could also be located on a track with many paths, and an entity might have a guidance system with various traits that may or may not help guide it to the proper direction. Up to this point, we have described how entities reproduce by making copies of themselves with mutations as a way of evolving. We can also use the concept of poly-parenting, where two or more entities can parent an offspring, with the specifics of traits having variance of how they express themselves such as dominant and recessive values or blends of parent traits with blend ratios as another trait.

The entities can also be nested within other entities and have multiple nested entities embedded within them. These nested levels can have symbiotic relationships with each other that can provide for a more efficient approach to generating many potential candidate solutions. Using our example condition, a race car produces exhaust that is proportional to its speed and distance travelled. Having fast cars that travel many paths might be a good way for many cars to utilize all of the available fuel, but they will produce a lot of exhaust. Outside of the cars specific functionality, we can account for the way in which the fuel is produced: a solar powered distillery whose output falls as smog levels rise. The car entities might also have a combustion sub-system that has variations in rate of fuel usage, power output and smog output, and further relationships to engine characteristics such as oxygen utilization (which can also be impacted by smog output), time to combustion, compression ratios, and other conditions which impact the size and weight of engine design. All of these characteristics can have multiple levels of abstraction and interdependency which can focus the problem solving simulation at desired scale. General models can be built with aspects of them set to specific variables or with limited variance, while other parts of simulation are run through the evolutionary computation simulation.

Examples of Complex Relations Among Data

These types of a variances and morphological relationships can be found in many complex data systems. Another example can be seen with human health data from large scale studies. Understanding how the many factors of human behavior, individual characteristics, diseases and treatments lead to patient outcomes is a daunting problem. Fortunately there is increasing data that begins to mark correlations between them. But this data has many hundreds or thousands of dimensions to it. For an individual patient, it isn't possible for them and their doctors to understand which changes might produce better outcomes. We can apply our multi-scale, environmental evolutionary approach to this dilemma. We can group different components of fitness into subsystems in a variety of ways, and look at how traits, some of which may exist in more than one subsystem, can lead to a holistic assessment of outcomes. For instance, we have extensive datasets that track people's lifestyle, family disease rates, and medical conditions with particular focus, such as heart disease, cancer, pulmonary disease, cognitive and neurological function and fitness. Large scale studies in each of these areas have all been done with different methodologies and produced results in a variety of formats, but in general they all have looked at many lifestyle traits such as: age, weight, height, sex, diet, medicine, supplements, heart rates, blood pressure, blood panels, sleep patterns, etc. Some studies have tracked hundreds of traits over tens of thousands of people over several decades. Others have tracked fewer variables over larger numbers of people over shorter times. Within each of these existing studies it is very difficult to utilize current analytical methods to determine what lifestyle one should pursue to produce optimal health outcomes. Should I take an aspirin a day or not? Does the amount of exercise that I do matter, or the amount of coffee that I drink, or the amount of time I spend watching TV? Will the aspirin improve my heart health but possibly increase my colo-rectal cancer risk?

In our evolutionary computing system, we can create a model of an individual's characteristics, to the extent that it known, and which can be continuously updated for both improving completeness and to include contemporaneous conditions. This model can be used as the basis for the creation of colonies of entities that can evolve variations that can be compared to outcomes derived from the datasets of these large scale studies as the multi-variant fitness conditions. The overall system can look at interrelationships between the various studies, and normalize the individual traits so that they can be compared across the board. It might show that optimizations for outcomes in one area might dramatically imperil one in another area.

Economics are another area that could be used with this methodology. Modeling the variations in micro and macro-economic conditions could help see possible consequences and solutions to policy or investment decisions. For instance, putting tariffs on a particular imported material might help boost a specific part of the economy, but it might also cause other parts of the economy to suffer. Many different industrial sectors can be modeled, each of which would have a variety of traits based on the price of production (materials, labor, energy, shipping, taxation) and income (prices, effort required, market size, competition). Data can be drawn from measured starting points and entities would be in many symbiotic interrelationships with each other, the characterization of which would also change over time.

Example Hardware Platforms

Figure 3:
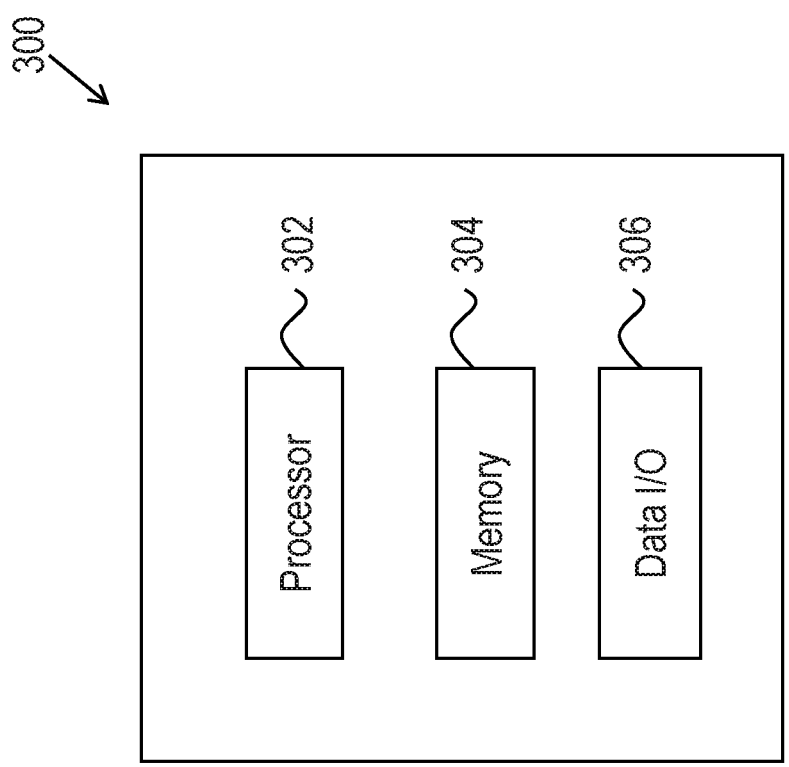
FIG. 3 is a block diagram of a hardware platform for implementing techniques described in the present document.

FIG. 3 shows an example hardware platform 300. One or more such platforms 300 may be used to implement the environment 100 described herein. In various embodiments, the platforms 300 may for a distributed computing system or may correspond to computing sources located in a computing cloud. The disclosed environment 100 is scalable for implementation on a single platform 300 that could be a mobile phone, a laptop or a workstation.

The platform 300 may include one or more processors 302. The processors 302 may be configured to execute code. The platform 300 may include one or more memories 304 for storage of code, data and intermediate results of execution. The platform 300 may include one or more interfaces 306 for data input or output. For example, the interfaces 306 may be a network connection such as a wired Ethernet or wireless Wi-Fi connection or may be communication ports such as USB, and the like. Various techniques described in the document may be implemented in a cloud based computing system where multiple hardware platform 300 may be present.

An Example of Simulation Environment

A simulation of this example system has been created to show how various data conditions can produce high performing outcomes. This simulation creates a multi-level environment with 3 levels of embedded systems. The level of embeddedness has no upper of lower limits. In this case we will name these levels the Assembly, the Amalgam, and the Environment. The Assemblies will be described in the most detail. They are artificial life entities, specified by a genetic code. This code specifies the number of nodes in an assembly and the ways in which nodes are arranged and connected to one another, and based on the location in the connection pattern, the function of each node. There are many Assemblies in an Amalgam. There is a symbiotic relationship between the colony of assemblies and the vitality of the amalgam. Amalgams capture energy from the environment that they are in, yet they can't utilize the energy until it has been metabolized by the Assemblies. Assemblies attempt to move through the amalgam to capture this energy, utilize it, and emit metabolites that the amalgam uses for its vitality.

Examples of Culling and Fitness Checking

Fitness checking and culling can take place at any of the hierarchy tiers. The fitness tests can have multiple factors and can be adjusted to allow for wider or narrower range of outcomes to pass. For instance, a fitness function of metabolic state might be used to cull Assemblies from the environment—if they are unable to add energy at a rate that matches or exceeds their utilization, they will cease to exist, and their particular configuration of data relations will not be a part of the overall set of possible data relationships going forward. If the fitness tests are applied at a higher level, such as the Amalgam level, a whole colony of underlying data relationships will be culled from the system. Other tests can that could be used would include the need to develop an excess of energy to allow an Assembly to combine with another one to produce offspring; Assemblies who are unable to produce offspring would leave the genepool. The data analysis system can run for an indefinite period, however we have found that over time, colonies will tend to reach a relative stasis of combinatorial possibilities, sometimes with more than one prevalent strain of data relations co-existing. These would then be good candidates to extract and examine the specifics of the data relationships to use as an aid to decision making processes.

Example Visualizations

Various figures provide examples of visual depictions of how the results obtained during the data analysis and evolution or relationships among Assemblies. One visualization technique may depict visual picture analogous to the development of various life forms in a colony through interactions, mutations and eliminations.

Table 1 shows an example of an amalgam format in which various Assemblies are defined with a simplified representation of the data used or processed and inputs and outputs to the Assemblies.

TABLE 1

Example Amalgam format

| Data | Input | Output |
| --- | --- | --- |
| Energy for Assemblies amount distribution | Energy into Amalgam for Assemblies from Environment | Produce metabolites for Environment |
| Metabolites for Amalgam vitality | From Assemblies | |
| Hydrostatic pressure | From Assemblies morphology, location and activity | Size of Amalgam Motion of Amalgam in Environment Together, allow it to bring energy into Amalgam for Assemblies |

Table 2 provides an example of Assembly format in which various sub-system of an Assembly mimic functionality of a simple lifeform and the corresponding data and input/outputs are used as functions that change the behavior and characteristics of an Assembly.

TABLE 2

Example Assembly format

| Sub-System | Data | Input | Output |
| --- | --- | --- | --- |
| | Cross product of motion from muscle nodes | From Muscle system From Environment conditions | Move Assembly |
| | Mating | From Metabolism | To Vision system to set mating flag |
| | Hydrostatic Field Morphology number of subsystem nodes Connectnome of nodes angles order Rules for expressing subsystems | From Assembly Morphology | To Amalgam Shell |
| | Metabolites % of metabolism utilization | | To Amalgam |
| Metabolism | Energy Utilization Rest Rate Active Rate | From all subsystems | To All subsystems |
| Vision | Width Depth Energy Use Energy Gain Energy Seen intensity degree off axis Mate intensity degree off-axis | From Environment From other entities From metabolism | To cognition node To metabolism |
| Cognition | Various vision nodes are weighted in summing to 1 Weighting is modulated over time Modulate output signal strength Modulate output signal targets | From Vision From Metabolism | To muscle nodes To metabolism |
| Motion | Energy available Utilization efficiency Impulse frequency Impulse intensity | From metabolism From cognition | Force and direction to Assembly |

Example Features and Platforms

Figure 4:
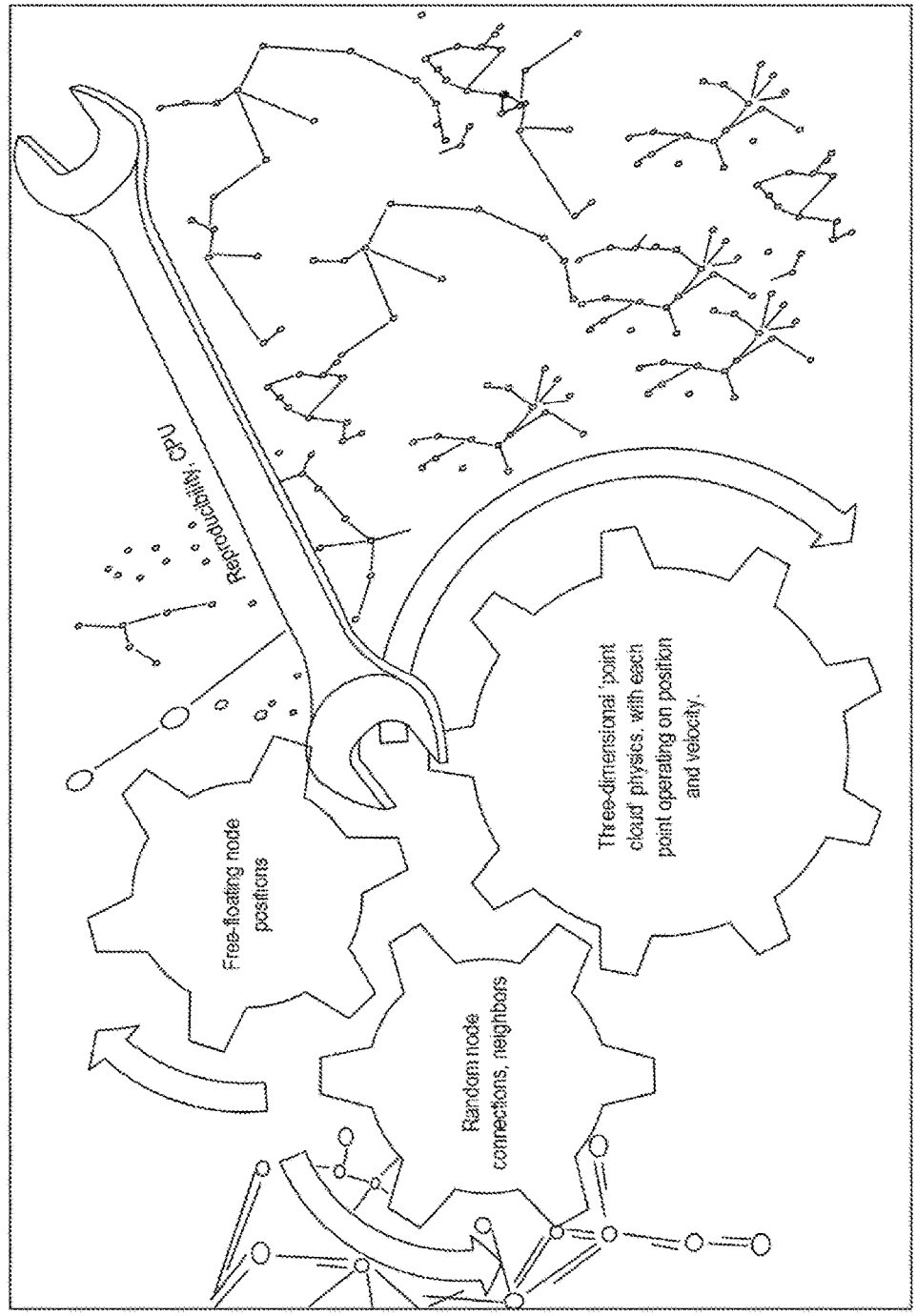
FIG. 4 shows an example system in which free-form floating point values are used for various computer data structures.

FIG. 4 shows an example system 400 in which free-form floating point values are used for various computer data structures. The system 400 may be analogized as an arrangement of interlocked gears whose movement, or computing progression, may be controlled separately, yet may be able to influence each other's movement (progression). For example, three "gears" or "subsystems" include a simulation of a three-dimensional point cloud physics model with each point within the cloud operating at a position and a velocity. The points may be connected to drive random node connections and neighbor selection based on their position/velocity values. The resulting computations may interact with free-floating node positions.

One of the big challenges in performing a meaningful analysis of complex data and making it useful to solving a certain problem is being able to visually present to a human user in a meaningful manner. In systems where data has tens or hundreds of attributes and may be analyzed for underlying complex relationship, the traditional database display techniques such as spreadsheets, filtered results and multi-dimensional graphs are inadequate because these techniques may visually overload the amount of information presented making it harder to notice. FIG. 4 shows an example of interactions between various components of the data analysis system as a number of interlocked gears to highlight the interaction between different node connections and positions. In one example aspect, these interactions may be advantageously use to display the results of ongoing simulations as "life forms" that evolve over the duration of simulation, interacting with each other, forming colonies, reproducing or detaching, mutating, and so on. Additional details of the various aspects of data analysis and visualization are also described with reference to FIGS. 5 to 11, as described next.

FIG. 5 shows examples of rigid grid structures and free-form structures while using integer representation for values used in various computer data structures. The structure on the left shows a solid closest-packing prism that represents a rigid (e.g., defined by connectivity to neighbors) integer based scheme of assembly structure. In this scheme, each point is represented with three integer numbers and each point or vertex of the grid differs from its neighbors in one attribute value. Compared to such a rigid structure, the one on right shows a computing platform in which the computations vertices are allowed to have a freedom to form and some of the resulting points are considered to be a part of the structure. The visual representation of the calculations on the right thus shows a scheme in which simulation results may take on many different values (not just along a rigid structure), and facilitate evolution of the simulation in a distributed manner. As visually depicted in FIG. 5, in one advantageous aspect, the display of data sets on the right is visually efficient and intuitive. In particular, data elements are spatially addressed and provide a visual status of the condition or evolution of data simulations.

Figure 6:
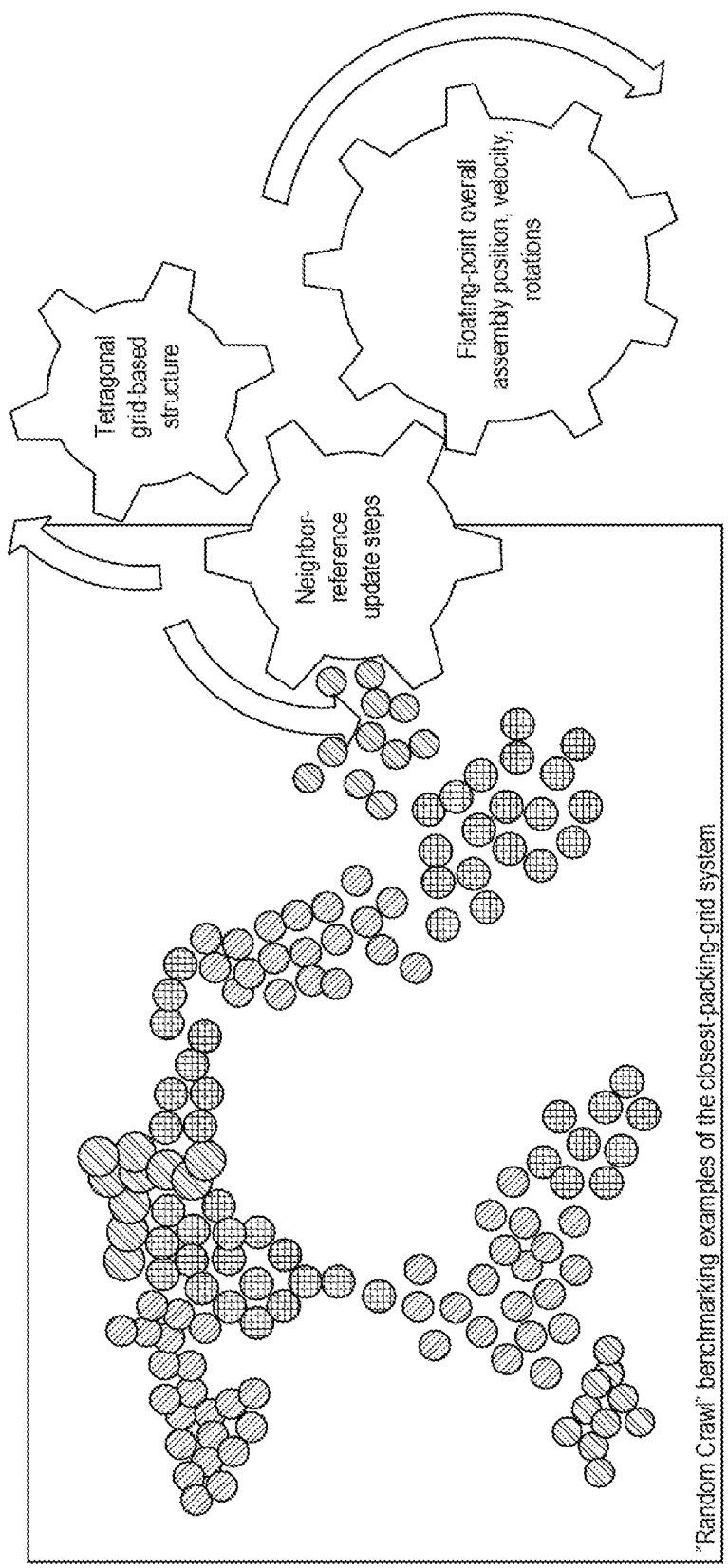
FIG. 6 is a pictorial depiction of the idea of performing calculations using a simpler calculation of structures.

FIG. 6 is a pictorial depiction of the idea of performing calculations using a simpler calculation of structures. FIG. 6 visually illustrates the operation of "random crawl" benchmarking examples of the closest packing grid system. Similar to FIG. 5, the visual depiction of FIG. 6 identifies structures and a human user can visually track the evolution of the structures (e.g., Assemblies) as the simulation progresses.

Figure 7:
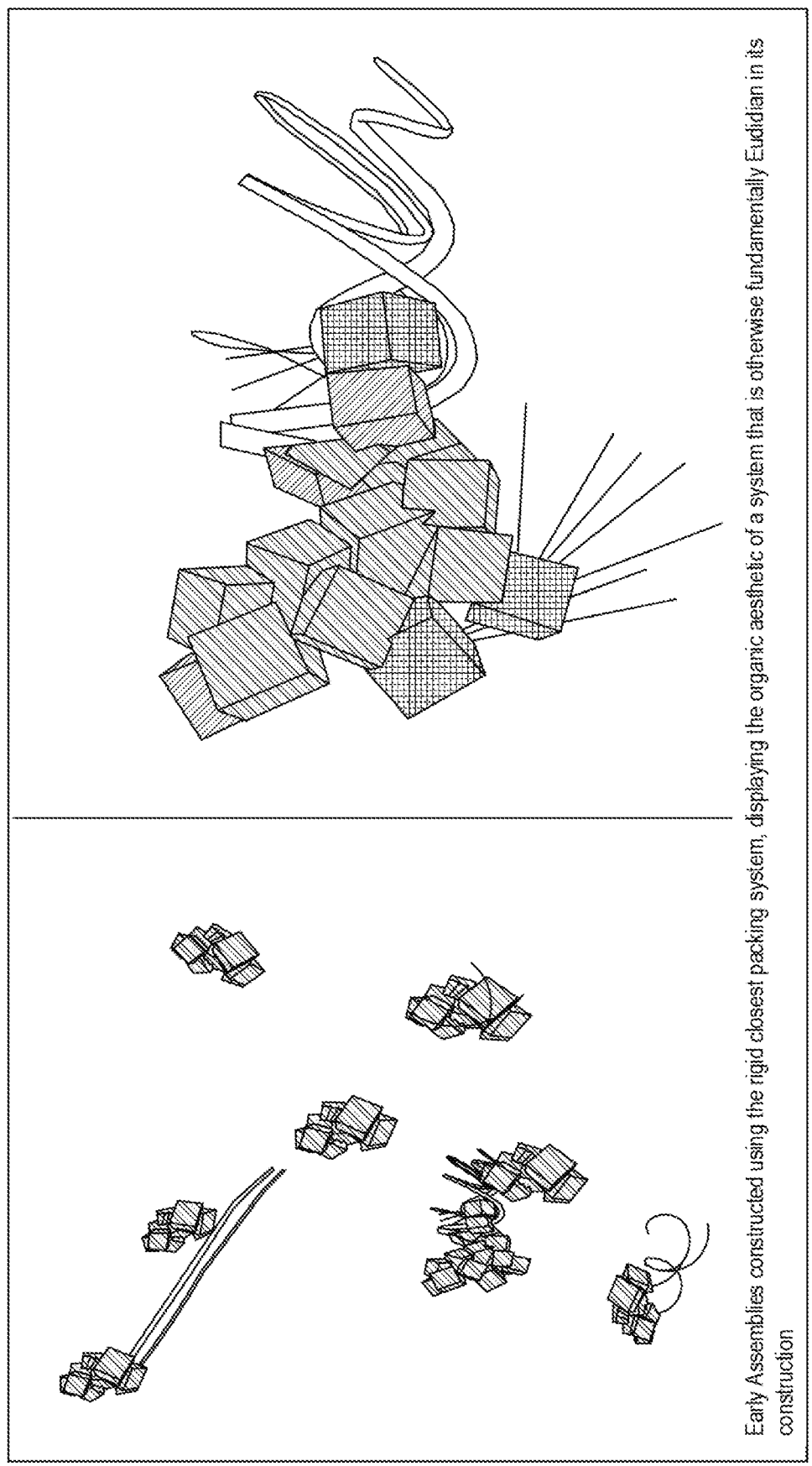
FIG. 7 shows an example visualization of intermediate results of computations in the program execution environment.

FIG. 7 shows an example visualization of intermediate results of computations in the program execution environment. In this example, each Assembly is constructed using a rigid closest packing grid system, displaying the organic aesthetic of the system that is otherwise Euclidean in its construction. The example in FIG. 7 shows how results of simulations can be visually depicted as living organisms or cells (e.g., the polyhedrons), with its corresponding connections to other data structures and evolution through the progression of data analysis.

Figure 8:
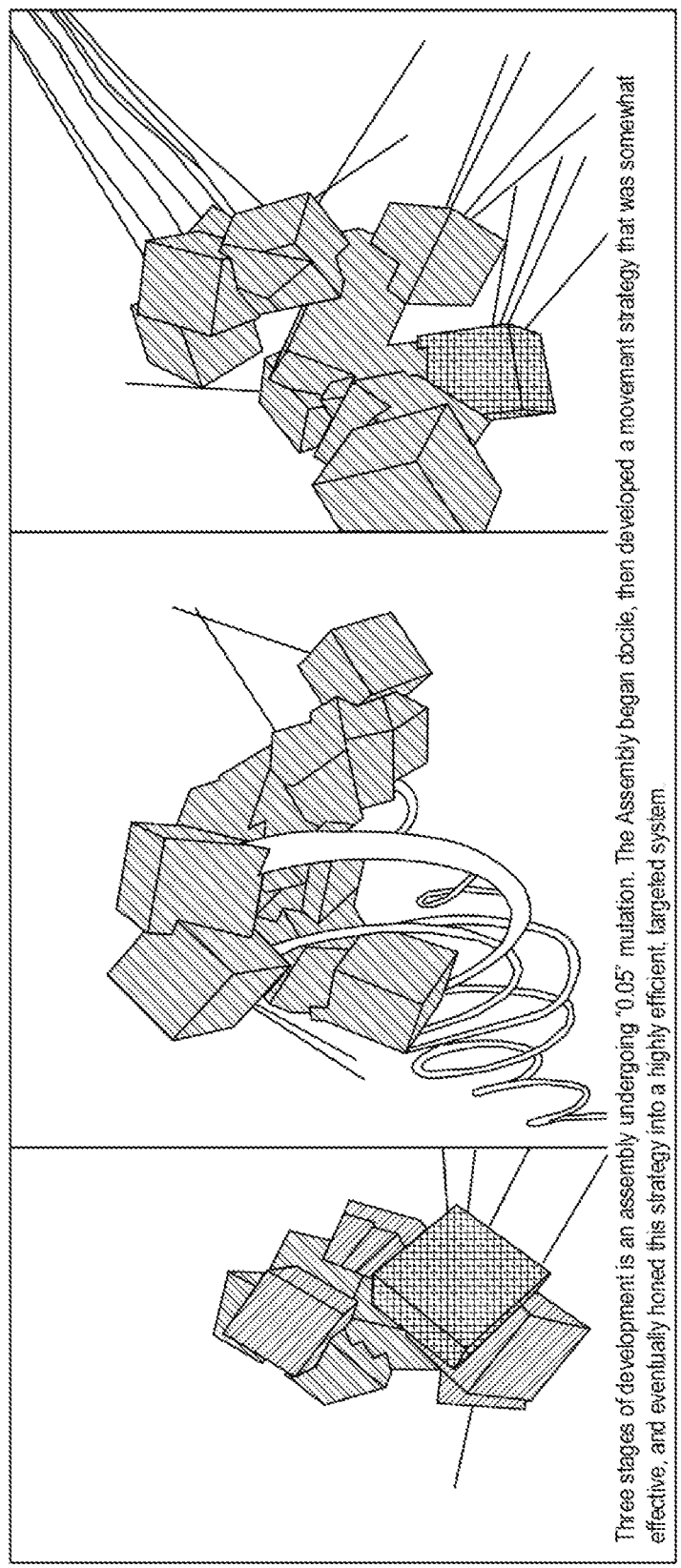
FIG. 8 is a pictorial depiction of an example of mutation of Assembly.

FIG. 8 is a pictorial depiction of an example of mutation of Assembly. In some example embodiments, a coefficient may be applied across variables of multiple types. This operation is difficult to balance and accordingly variables are evaluated on a maximum change scale, relative to their current values. The three stages of computations (from left to right) are shown to undergo a mutation in which the Assembly begins as a docile structure, then develops a movement strategy that was effective, and eventually hones the strategy in a highly efficient targeted system. As depicted in FIG. 8, a single entity (a collection of multiple cubes, each having a different visual identity or gray-scale representation to distinguish its identity from others), may evolve into a more complex entity (middle) and develop relationships among various components, including using mutation process, gradually resulting in the entity on the right. This may be called "0.05" mutation based on the operational parameter designed to create changes from one iteration to next, e.g., as disclosed in the present document.

Figure 9:
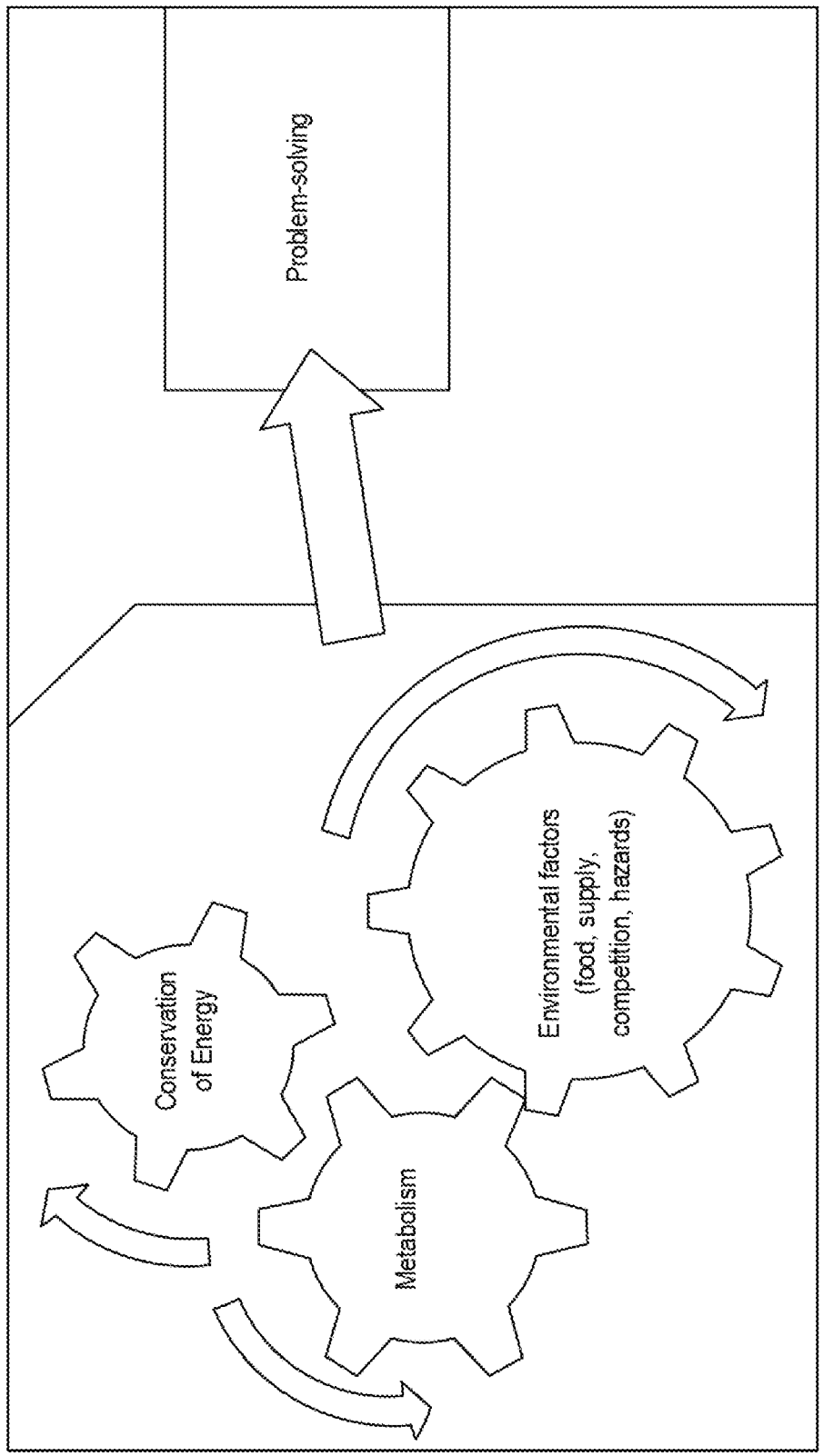
FIG. 9 is a pictorial demonstration of an example of influence of environmental factors on calculations.

FIG. 9 is a pictorial demonstration of an example of influence of environmental factors on calculations. Some embodiments disclosed herein may use the concept of evolution as understood in the biological world both for performing complex data analysis and for providing a visual display of intermedia results during the complex data analysis. For example, a real-world problem may be posed as a biological problem. Analogous to the evolution of biological life where the governing laws include laws of nature such as conservation of energy, and biological life is limited and defined by its own metabolic activity, and growth and changes to biological life forms are influenced by environmental factors such as food supply, competition with other biological life forms, hazardous conditions, and so on, evolution of data objects may be simulated into a similar framework to solve problems. In such as framework, as described throughout this document, real life problems may be posed as data characteristics or relationships or correlations, and the corresponding starting data set may be allowed to evolve using the "rules of nature," "rules of life (e.g., metabolism)" and "rules of environment" that define the complex relationship among various data objects and the interactions among them.

Figure 10:
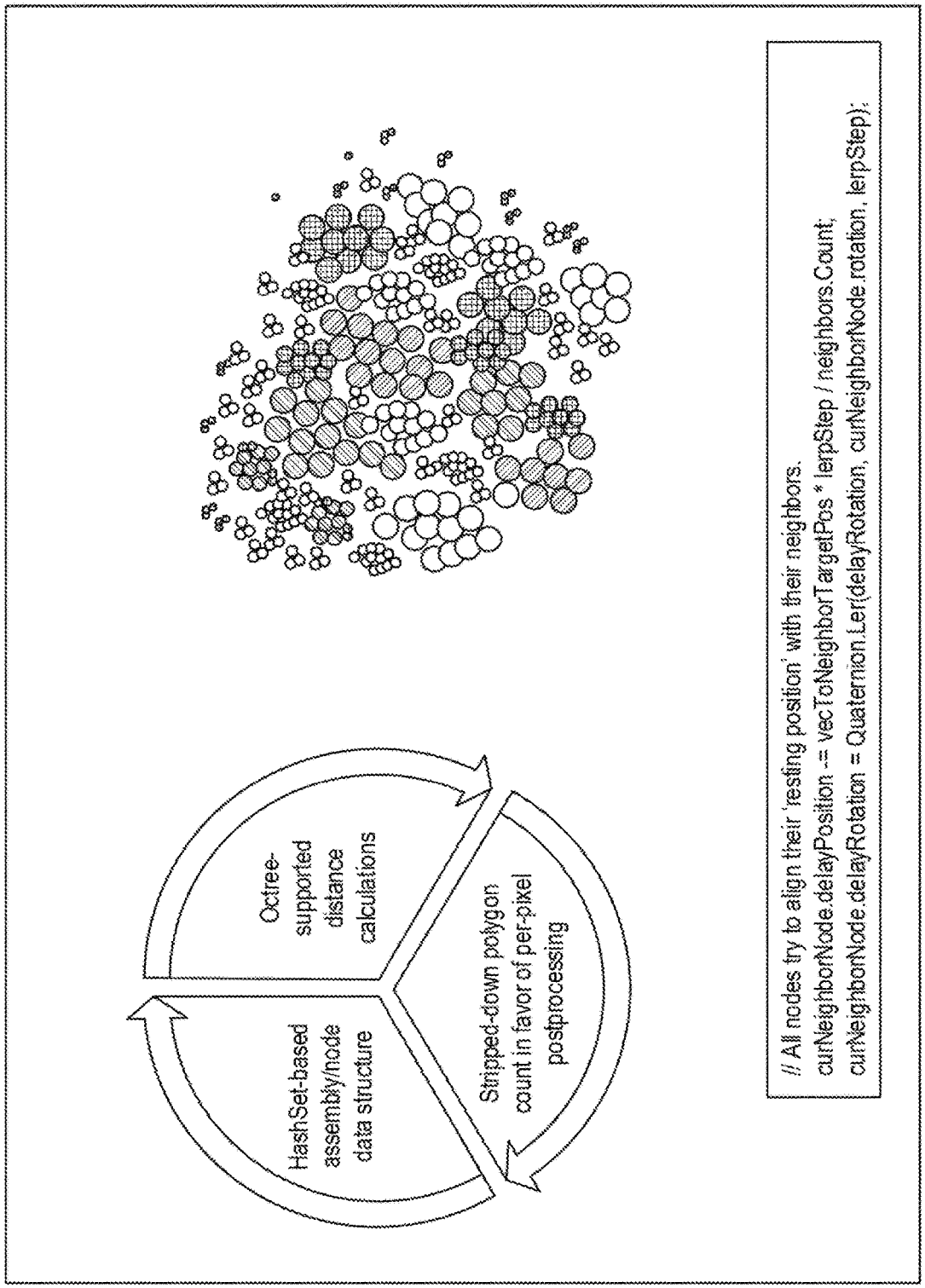
FIG. 10 shows an example process of optimization of the computing system.

FIG. 10 shows an example process of optimization of the computing system that is operating as a data analysis system. FIG. 10 shows an engine optimized to run on 10,000+ individual network nodes. A simulation of complex data may have to be optimized to keep the computational complexity in control and real-time. One such method may include the use of an octrees, as depicted in FIG. 10. For example, the universe of all data sets undergoing evolution at a given time may be divided into eight octants (any number, in general). From the division, a smaller set of entities or data objects that have possibility of effectively affecting the final outcome may be selected for retention and the remaining data entities may be "let go" or eliminated. A metric such as distance of neighbors may be used for this culling. For example, distances may be compared to a threshold and data entities having a distance longer than the threshold may be de-emphasized or eliminated. A similar strategy may be used for both culling of data objects and also culling of computational nodes that are implementing the evolution of data objects.

As depicted in FIG. 10, internodal physics interactions operate on a 'neighbor-based' system. Each node has baked references to its neighbors, and then attempts to 'pull' itself to the target position relative to the neighbor. The neighbor also performs the same operation. Once all nodes have run their calculations, positions and velocities are updated for that frame.

For example, in some embodiments, nodes may implement the following logic to try to align their 'resting position' with their neighbors.

curNeighborNode.delay
    Position-=vecToNeighborTargetPos*lerp Step/
    neighbors.Count;

curNeighborNode.delayRotation=Quaternion.Ler(delayRotation, curNeighborNode.rotation,lerpStep).

Here the variables suffixed Position and Rotation may represent position and rotational angle in a 3D space of the node with respect to a coordinate axis. For example, a convenient 3D reference axis system may be from viewpoint of a user of the simulation system. Furthermore, the position may be adjusted using a vector to a neighboring target position in steps of lerpStep variable, which is scaled by a count of number of neighboring nodes. For example, when number of neighboring nodes is large, e.g., when a given node is in a crowd, then the position adjustment may correspondingly scaled down or slowed down. This mathematical property may thus facilitate stable conversion of simulations. The second equation above describes rotational movement of nodes in a quaternion coordinate system (four-dimensional complex number system) in which rotation is achieved based on a relationship with neighboring node rotation after a certain delay. For example, this mathematical relationship allows neighboring datasets to be influenced by each other's changes after passage of certain amount of delay (e.g., number of iterations). Each "dot" in FIG. 4 or solid geometries such as circular nodes or cubes in FIGS. 5 to 11 may represent an entity, or a collection of data sets and relationships.

In some embodiments, closest-packing grid system may be used as the deterministic method for saving/restoring/mutating assembly structure, but the 'lattice' is no longer rigid. New nodal physics engine may pull from soft body physics engine fundamentals to allow for flowing, organic structures that can simulate organic tissue and muscle.

For simulation, and for visually displaying results, motion is achieved by the product of muscle contraction vs. resultant muscle displacement and the frequency of these contractions. Differences in resultant motions is observable in the simulation.

Figure 11:
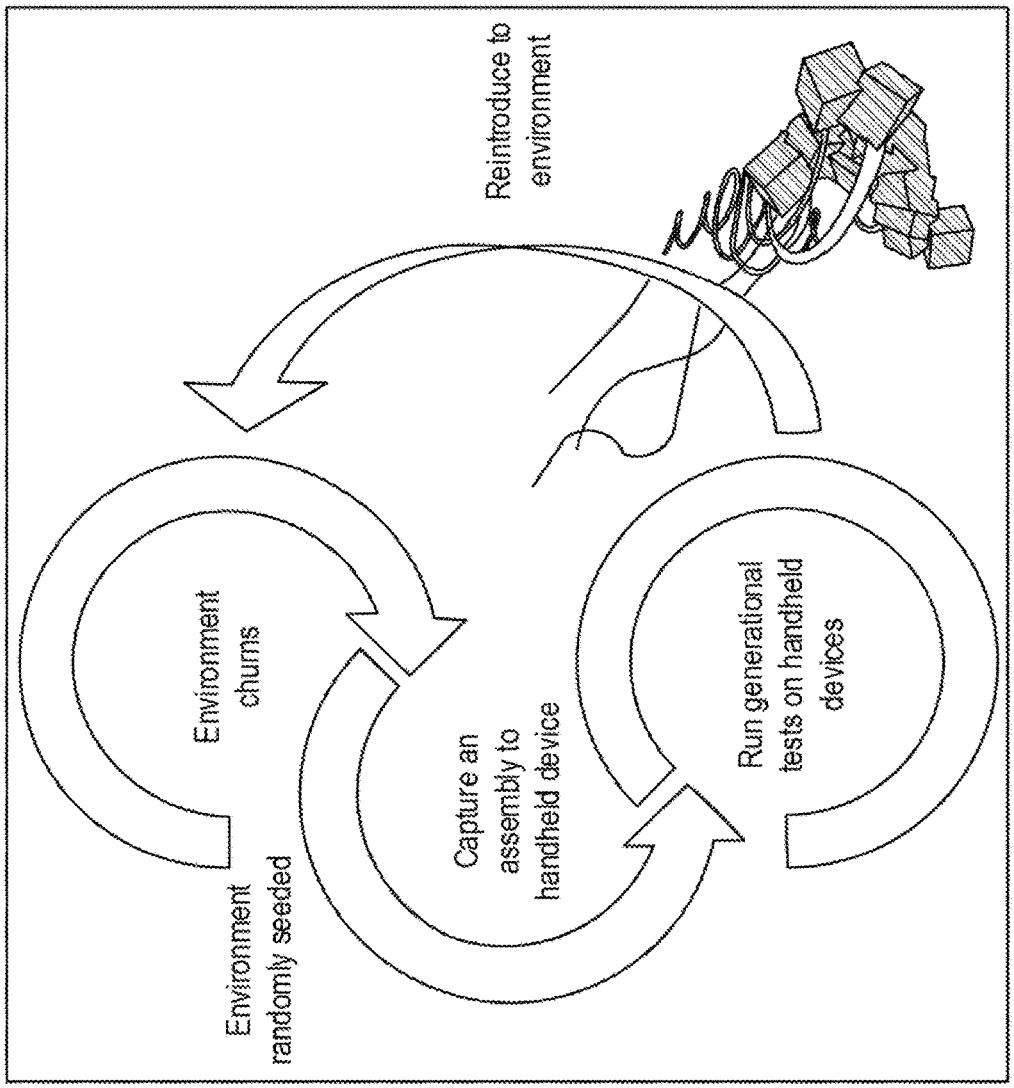
FIG. 11 shows an example of asymmetrical cross-platform implementation.

FIG. 11 shows an example of asymmetrical cross-platform implementation. Starting from top left, an environment of various Assemblies may be randomly seeded with starting data entities. As the environment churns (evolves), some of the evolved assemblies may be transferred to another computational platform that was previously not a part of the simulation framework. This receiving computational platform may be, for example, a handheld device such as a tablet or a smartphone. The simulation may continue on this device in isolation from the simulation running on the starting data objects. During the simulation on the handheld device, simulation may progress using slightly different parameters for certain environmental factors (e.g., power consumption). At some future time, the results of the handheld device simulation may be reintroduced back to the original or the principal simulation environment.

With environmental conditions reintroduced, the simulation returns to the 'soup' simulation previously run with the rigid assemblies, but now with higher performance as well as more interesting physics-based assembly behaviors.

Examples of Reproduction

While the environment is seeded with randomly-generated unique assemblies, two assemblies with high enough internal energies may attempt to reproduce sexually. The offspring will contain structural and nodal information based on a random inheritance from both parents, plus a small amount of random mutation.

Examples of Increased Complexity

The highest-level stage of the environment, 'Utopia', serves to bring the concepts and machinations of the earlier stages into a social context. The user operates a humanoid form with some form of gross interaction with the environment, which has grown out of (and built upon) the processes that generated the first and second levels.

Figure 12:
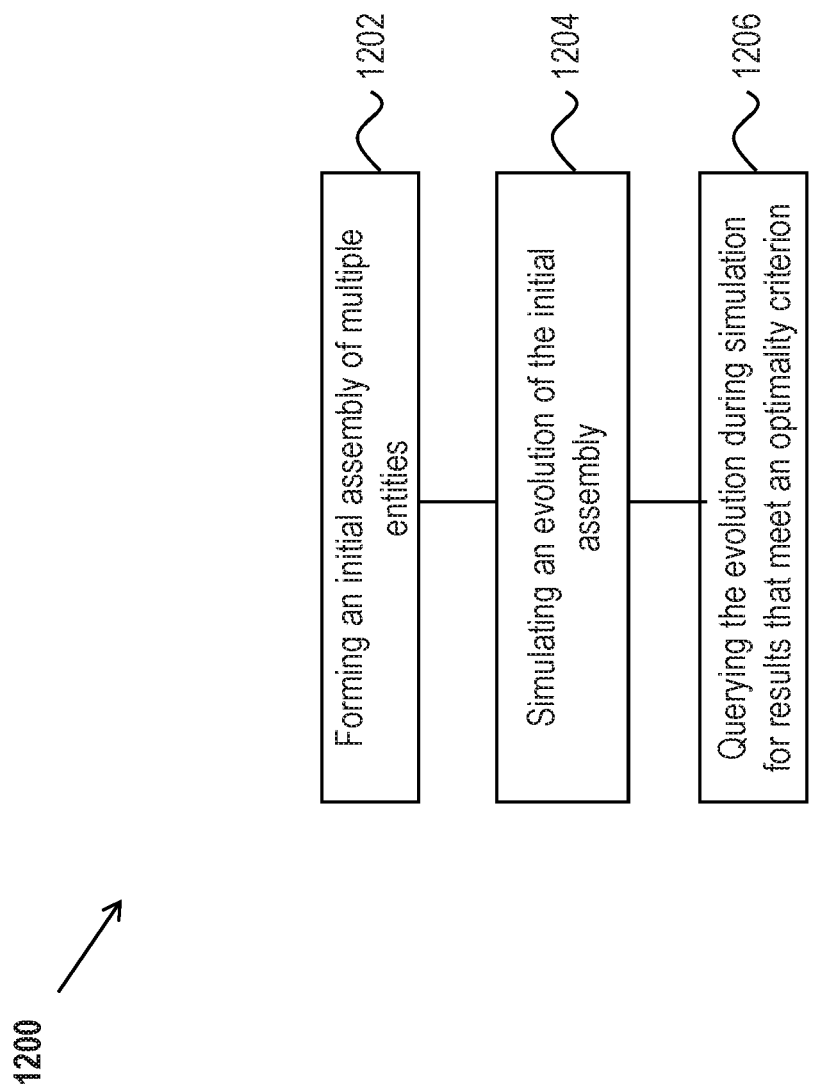
FIG. 12 is a flowchart of an example method of complex data analysis.

FIG. 12 is a flowchart representation of an example method 1200 of data processing and analysis. The method 1200 may be implemented by a data analysis system described in the present application, e.g., using the hardware platform described with respect to FIG. 3.

The method 1200 includes, at 1202, forming an initial assembly of datasets comprising multiple entities, where each entity is a collection of variables and relationships that define how entities interact with each other.

The method 1200 includes, at 1204, simulating an evolution of the initial assembly by performing multiple iterations in which a first iteration uses the initial assembly as a starting assembly. The simulation of the evolution in operation 1204 may include a first operation of causing the starting assembly to evolve by having the multiple entities in the starting assembly (1) interact with other entities in the starting assembly using the relationships; or (2) change values of variables using a randomization technique, a second operation of culling, at an end of an iteration, a number of multiple entities that fail to meet a target objective function for that iteration, and a third operation of replacing, selectively based on finality of the multiple iteration, the starting to include remaining entities after the culling.

The method 1200 includes, at 1206, querying, during the simulating, the evolution of the initial assembly, for datasets that meet an optimality criterion.

The method 1200 may further be used to model dependencies between different parts or sub-systems. Dependencies may be defined between different sub-systems that becomes "genes" of the corresponding assembly entities. Interactions among the multiple genes becomes behavior of the assembly. In some implementations, a real-life problem for data simulation and analysis may be mapped to its corresponding assemblies, which may serve as a starting point for a simulation of behavior of the system.

During the simulating, the evolution of the initial assembly may be determined using a fitness function and by reading out characteristics of the assembly at a given time. In principal, the simulation may not have a well-defined end criterion. For real world simulations, the results of the querying may be used to end the simulation as it may produce an answer of interest.

In some embodiments, an entity may itself represent a collection of other entities (e.g., a human body is a collection of multiple organs, which are a collection of multiple cells, and so on.)

In some embodiments, different target objective functions may be used for different iterations. In some implementations, an objective function may be based on same parameters, but have different values in different iteration. For example, entity dimension may be used as the objective function criteria and the threshold of dimension may change from one iteration to next. Alternatively, or in addition, different iterations may use different parameters for the objective function. For example, entity dimension may be used in one iteration, while entity weight may be used in the objective function for another iteration. In some cases, the objective function may use a combination of multiple entity parameters.

As further described in the present document, entities may be able to create (give birth to) new entities as a result of interactions between them. For example, starting from a patient birth year entity and a patient weight entity, when simulation reaches a stage where a correlation between a specific weight and birth year reaches a significant number, a new entity may be created that corresponds to "obese teenagers." This new entity may be defined with its own data structures and functions (e.g., increased sensitivity to sugar intake).

In some embodiments, new entities may be created through a dataset mating process. This process may occur when assemblies have a surfeit of energy reserves, and they are able to turn some of their activity toward the search for an appropriate mate in addition to their search for energy input. The energy may represent a trait determined through their genetic codex and a condition that is met by their metabolic activity and environmental interactions. When two (or more) assemblies find mates of interest, they are able to create new entities—offspring—which have a mix of traits from each parent. The mix itself may be something that has evolutionary variation as with all other traits of the assembly. The mixing may involve mathematical techniques such as linear weighting, non-linear weighting or randomization. In some cases, it may be possible to automatically generate new entities from more than two parent entities. For example, during the process of dataset mating, one parent entity may find more than one other entities suitable for the creation of a new entity. Depending on a trait of this parent entity, e.g., whether or not this parent entity can generate new entities by mating with multiple other entities, the above-described techniques may be used to create new entities with multiple parents. One advantage aspect of such a multi-parent data analysis technique is that by controlling the number of parents that can lead to new offspring entities, the amount or range of variations in datasets from one generation to next, or one iteration to next, can be controlled.

For example, in some embodiments, the characteristics of parent entities A and B (or additional parents, if any)—which include specific data values as well as the specifications of algorithmic methods are inherited by the new entities—C, D, E, etc. The total number of new entities created may be a variable that can be set with upper and lower limits and with a control over the possibilities of a number of offspring being created such as a fixed number, a random number, a random number that has a probabilistic outcome. The expression of specific traits from either parent can have a variety of possibilities, these possibilities themselves are an inheritable and mutable trait. One parent's version or dataset can be directly copied to one of the offspring, some mixture of traits can occur that combines aspects of parents' traits and the weighting of that combination is itself an inheritable characteristic, and any of this can be subject to a mutation, where whichever method is being used, the outcome could have a randomization factor applied to it. The randomization factor may be external to the genetic code, and may be set by the human operating the system and it can be set to have its own distribution over the system, such as the same mutation factor applied to entire colony, or a varying mutation factor applied to each member of the colony, or a mutation factor that has a particular variance rate over different generations of the colony. For example, a mutation rate of 10% of genes mutating with 10% variation of data traits in the initial generation may be specified and each succeeding generation the mutation rate goes down by 1%. These mutation rates can also be limited to specific areas of the genetic code, as determined by the operator of the simulation system.

In some embodiments, at least some entities in the initial assembly correspond to a real-world attribute and wherein the forming the initial assembly of datasets includes forming the at least some entities by including fields of a database based associated with the real-world attribute. Various examples of real-world problems are described in the present document for illustration, and other applications may also be possible.

Figure 13:
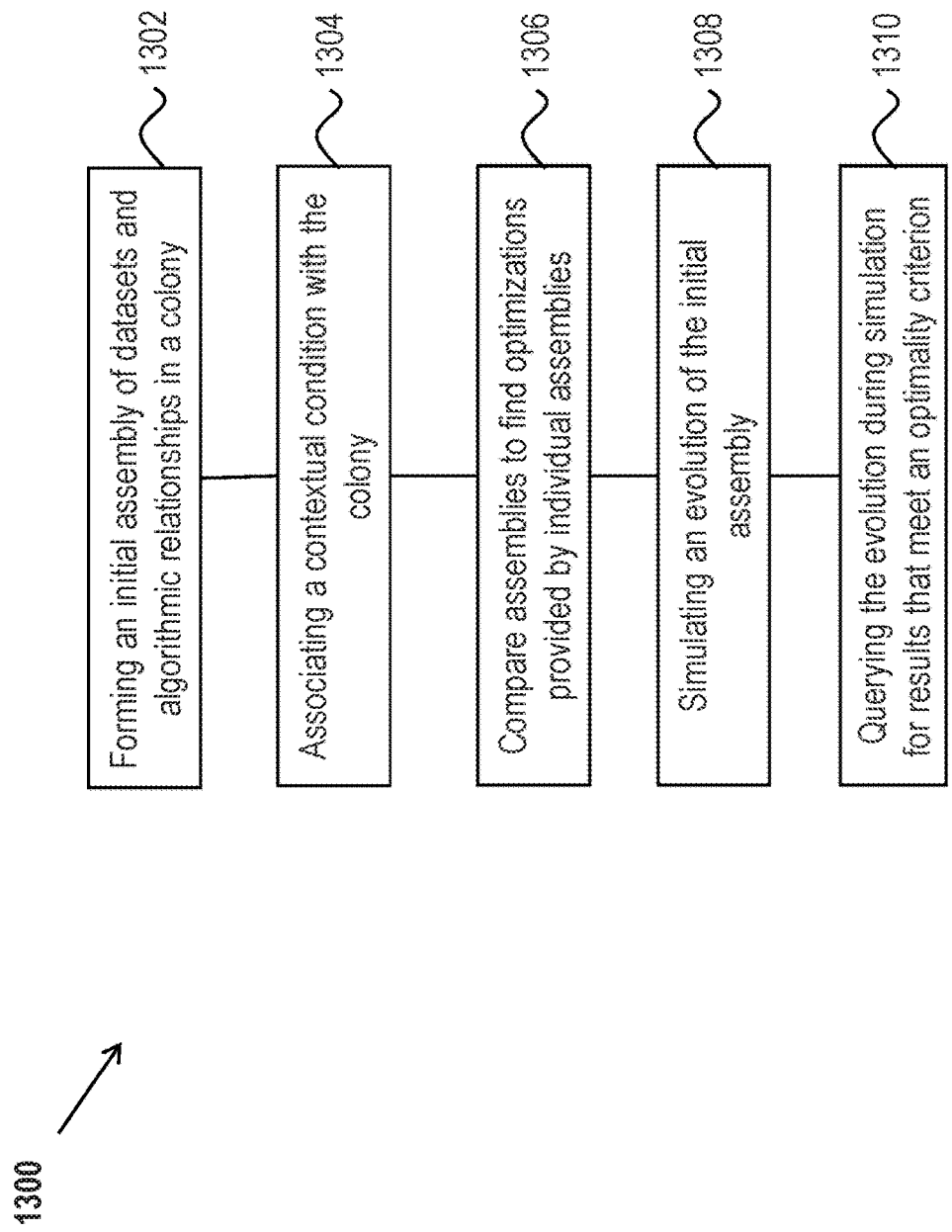
FIG. 13 shows a flowchart of another example method of complex data analysis.

FIG. 13 is a flowchart of another example method 1300 for analyzing complex data. In some embodiments, the method 1300 includes forming an initial assembly of datasets and algorithmic relationships by instantiating in a colony of assemblies that have a range in variations of their dataset and algorithmic conditions. The method 1300 may be implemented by a data analysis system using a hardware platform such as described with respect to FIG. 3.

In some embodiments, the method 1300 includes associating at least one contextual condition with the colony. For example, the contextual condition associated with the colony may be set up to have the data sets get into a competition during the simulation.

In some embodiments, the method 1300 includes comparing individual assemblies in the colony against each other and with the at least one contextual condition to find optimizations provided by the individual assemblies. For example, the comparing operation may be used to find particular optimizations provided by individual assemblies. A particular optimization may be, for example, formulated in terms of meeting some target value or values of an objective function. The target objective functions may be changed for different iterations. Therefore, one individual assembly may be deemed to be optimal at one iteration but may not be considered optimal at another iteration before or after that iteration.

In some embodiments, the method 1300 includes simulating an evolution of the initial assembly by performing multiple iterations in which a first iteration uses the initial assembly as a starting assembly. The simulation may be performed by causing the starting assembly to evolve by having each dataset in the starting assembly to (1) interact with other datasets in the starting assembly using corresponding algorithmic relationships; or (2) change values of at least some datasets using a randomization technique, culling, at an end of an $n^{th}$ iteration, assemblies in the colony that failed to meet a target objective function for the $n^{th}$ iteration and replacing, selectively based on finality of the multiple iterations, the starting assembly to include remaining datasets and algorithmic relationships after the culling.

With respect to the methods 1200 and 1300, For example, an initial assembly may be formed based on a template provided by an operator of a data analysis system and by reading entries of one or more databases. The databases may have similar data (e.g., databases of two medical or financial institutions) or may include dissimilar data (e.g., medical database and financial database). The initial assembly may be formed based on a set of rules that are specified by an operator.

With respect to the methods 1200 and 1300, the simulation of the evolution may be performed in an iterative manner. In some embodiments, various datasets and assemblies may be iteratively evolved in a non-synchronous manner. For example, one assembly may iterate K number of times over a period while another assembly iterates L number of times during the same period, with K and L being different integers.

With respect to the methods 1200 and 1300, the datasets in assemblies may interact with each other using algorithmic relationship based on meeting a compatibility criterion. For example, a first dataset may check a certain property of a second dataset and then use the second dataset for its evolution only if the second dataset is found to be compatible. Various compatibility criteria may be used in different embodiments, in different iterations or by different datasets. A compatibility criteria rule may be pre-specified for the simulation of the evolution or may be specified and evolve during the simulation. Alternatively, the compatibility criteria may be defined as another entity or assembly in the simulation and may have its own life during the simulation. Some examples of compatibility criteria include—a number of iterations that the second dataset has undergone. For example, a dataset that has undergone a number of iterations or evolutions greater than a threshold may be de-emphasized or used with a reduced probability for evolution of the first dataset (e.g., because it represents past happenings). Alternatively, in some embodiments, a dataset that has undergone fewer evolutions may be used more often or with a higher weight. Such a compatibility rule may be used for speeding up convergence of the iterations by conforming to older iterations.

With respect to the methods 1200 and 1300, the culling operation may include comparing individual entries of an assembly with a template and removing assemblies that deviate from the template. Alternative, or in addition, a function that uses some (or all) entries of the assembly may be evaluated. A check may be performed on the value of the function being within a certain range, and if not, then the corresponding dataset or assemblies may be removed from further consideration during the evolution. For example, the function may evaluate "energy" of the assembly (e.g., magnitudes) or "vitality" of the assembly (e.g., how many other assemblies were modified due to this assembly, or how many other assemblies have caused changes to this assembly), or "uniqueness" of the assembly (e.g., is this assembly similar to at least N other assemblies, where N is a threshold), and so on. The function may therefore cause an outlier to be eliminated (or alternatively promoted, if mutations of data are desired). The function may, for example, be defined to eliminate insignificant assemblies or assemblies that are not in a family. Alternatively, a function may be designed to reduce chances of conglomeration of similar looking datasets. Thus, selection of which functions to use for culling may be effectively used to steer the evolution in a desired direction of convergence. In some embodiments, the functions may be pre-defined by a user of the data analysis system. In some embodiments, rules may be defined for evolving the functions themselves during the simulation. For example, if the number of iterations goes beyond a threshold and convergence is still not obtained, the culling function may be altered to facilitate faster convergence.

The methods 1200 and 1300 may also provide snapshots of ongoing evolution to a user to allow a user to monitor and/or control evolution and data analysis. For example, the datasets that meet an optimality criterion may be provided as a response to a query. The query may be an explicit query received at a user interface of the simulation system. Alternatively, or in addition, the query may be implicit, e.g., based on passage of time or based on occurrence of a specific event (e.g., a new assembly or a new colony is created).

In some embodiments, the evolution of the initial assembly may be continuously provided to a user interface. FIGS. 4 to 11 provide various examples of visualization techniques used to provide information about evolution of assemblies, colonies, amalgams and environments.

In some embodiments, the above described techniques, including methods 1200 and 1300, may be a simulation system that is implemented on one or more hardware platforms, e.g., as described with respect to FIG. 3.

In some embodiments, the above-described techniques may be embodied in the form of processor-executable code and stored on a program medium that can be read by a computer for implementing the data analysis methods described herein.

From the above description, it will be clear for one of skill in the art that novel techniques for analyzing complex data sets and discovering relationships among them are disclosed. The disclosed techniques may be executed on a single computer platform, or a group of computing platforms such as a network or a cloud computing platform, or be implemented on a platform, transferred to another platform and re-introduced back on the original platform.

It will further be appreciated that, in some embodiments, the data analysis may mimic evolution of life forms, both in terms of the rules of analysis and also for displaying the intermediate results. The amalgam, for example, may represent a high level collection of multiple assemblies that may represent lowest level life forms (e.g., single cell life). The visual depiction of evolution of data analysis provides an intuitive was by which a human user is able to keep track of intermediate results of the analysis and control the flow of analysis.

It will further be appreciated by one of skill in the art that the techniques disclosed in the present document may be used to analyze complex datasets to discover or formulate relationships among various datasets. The analysis is performed iteratively such that various dataset relationships are formulated, evaluated and propagated or discarded based on certain objective functions.

Implementations of the subject matter and the functional operations described in this patent document and attached appendices can be implemented using data processing units that include various systems, digital electronic circuitry, or in computer software, firmware, or hardware, including the structures, modules and components disclosed in this specification and their structural equivalents, or in combinations of one or more of them. Implementations of the subject matter pertaining to data processing described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit", "data processing module", or "data processing apparatus", or the like, encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

The invention claimed is:

1. A computer-implemented data processing method, comprising:
    forming an initial assembly of datasets and algorithmic relationships by instantiating in a colony of assemblies that have a range in variations of their dataset and algorithmic conditions;
    associating at least one contextual condition with the colony;
    comparing individual assemblies in the colony against each other and with the at least one contextual condition to find optimizations provided by the individual assemblies;
    simulating an evolution of the initial assembly by performing multiple iterations in which a first iteration uses the initial assembly as a starting assembly, including:
        causing the starting assembly to evolve by having each dataset in the starting assembly to (1) interact with other datasets in the starting assembly using corresponding algorithmic relationships; or (2) change values of at least some datasets using a randomization technique;
        culling, at an end of an $n^{th}$ iteration, assemblies in the colony that failed to meet a target objective function for the $n^{th}$ iteration; and
        replacing, selectively based on finality of the multiple iterations, the starting assembly to include remaining datasets and algorithmic relationships after the culling; and
    providing, based on a query during the evolution of the initial assembly, datasets that meet an optimality criterion.

2. The method of claim 1, wherein the comparing is used to find particular optimizations provided by individual assemblies.

3. The method of claim 1, wherein a different target objective function is used for at least some iterations.

4. The method of claim 1, wherein the target objective function includes an energy function.

5. The method of claim 1, wherein the target objective function includes a uniqueness function.

6. A computer implemented data processing method, comprising:
    forming an initial assembly of datasets comprising multiple entities, where each entity is a collection of variables and relationships that define how entities interact with each other;

simulating an evolution of the initial assembly by performing multiple iterations in which a first iteration uses the initial assembly as a starting assembly, including:
    causing the starting assembly to evolve by having the multiple entities in the starting assembly (1) interact with other entities in the starting assembly using the relationships; or (2) change values of variables using a randomization technique;
    culling, at an end of an iteration, a number of multiple entities that fail to meet a target objective function for that iteration; and
    replacing, selectively based on finality of the multiple iterations, the starting to include remaining entities after the culling; and
querying, during the simulating, the evolution of the initial assembly, for datasets that meet an optimality criterion.

7. The method of claim 6, wherein at least one of the multiple entities includes a collection of entities.

8. The method of claim 6, wherein a different target objective function is used for at least some iterations.

9. The method of claim 6, wherein the operation of causing the starting assembly to evolve further includes creating new entities as a result of interaction between two of the multiple entities.

10. The method of claim 6, wherein at least some entities in the initial assembly correspond to a real-world attribute and wherein the forming the initial assembly of datasets includes forming the at least some entities by including fields of a database based associated with the real-world attribute.

11. A computing system comprising one or more hardware platforms configured to implement a method, comprising:
    forming an initial assembly of datasets and algorithmic relationships by instantiating in a colony of assemblies that have a range in variations of their dataset and algorithmic conditions;
    associating at least one contextual condition with the colony;
    comparing individual assemblies in the colony against each other and with the at least one contextual condition to find optimizations provided by the individual assemblies;
    simulating an evolution of the initial assembly by performing multiple iterations in which a first iteration uses the initial assembly as a starting assembly, including:
        causing the starting assembly to evolve by having each dataset in the starting assembly to (1) interact with other datasets in the starting assembly using corresponding algorithmic relationships; or (2) change values of at least some datasets using a randomization technique;
        culling, at an end of an $n^{th}$ iteration, assemblies in the colony that failed to meet a target objective function for the $n^{th}$ iteration; and
        replacing, selectively based on finality of the multiple iterations, the starting assembly to include remaining datasets and algorithmic relationships after the culling; and
    providing, based on a query during the evolution of the initial assembly, datasets that meet an optimality criterion.

12. A computer program product having code stored thereon, the code, when executed by a processor, causing the processor to implement a method, comprising:
    forming an initial assembly of datasets comprising multiple entities, where each entity is a collection of variables and relationships that define how entities interact with each other;
    simulating an evolution of the initial assembly by performing multiple iterations in which a first iteration uses the initial assembly as a starting assembly, including:
        causing the starting assembly to evolve by having the multiple entities in the starting assembly (1) interact with other entities in the starting assembly using the relationships; or (2) change values of variables using a randomization technique;
        culling, at an end of an iteration, a number of multiple entities that fail to meet a target objective function for that iteration; and
        replacing, selectively based on finality of the multiple iterations, the starting to include remaining entities after the culling; and
    querying, during the simulating, the evolution of the initial assembly, for datasets that meet an optimality criterion.

13. The computing system of claim 11, wherein the comparing is used to find particular optimizations provided by individual assemblies.

14. The computing system of claim 11, wherein a different target objective function is used for at least some iterations.

15. The computing system of claim 11, wherein the target objective function includes an energy function.

16. The computing system of claim 11, wherein the target objective function includes a uniqueness function.

17. The computer program product of claim 12, wherein at least one of the multiple entities includes a collection of entities.

18. The computer program product of claim 12, wherein a different target objective function is used for at least some iterations.

19. The computer program product of claim 12, wherein the operation of causing the starting assembly to evolve further includes creating new entities as a result of interaction between two of the multiple entities.

20. The computer program product of claim 12, wherein at least some entities in the initial assembly correspond to a real-world attribute and wherein the forming the initial assembly of datasets includes forming the at least some entities by including fields of a database based associated with the real-world attribute.

\* \* \* \* \*